US011172701B2

(12) United States Patent
Richmond et al.

(10) Patent No.: US 11,172,701 B2
(45) Date of Patent: Nov. 16, 2021

(54) SYSTEM UTILIZING COMPRESSED SMOKABLE PRODUCT

(71) Applicant: BANANA BROS, LLC, Culver City, CA (US)

(72) Inventors: David Richmond, Culver City, CA (US); Howard Richmond, Los Angeles, CA (US); Manuel A. Montano, Gardena, CA (US)

(73) Assignee: Banana Bros, LLC, Culver City, CA (US)

( * ) Notice: Subject to any disclaimer, the term of this patent is extended or adjusted under 35 U.S.C. 154(b) by 0 days.

(21) Appl. No.: 15/627,318

(22) Filed: Jun. 19, 2017

(65) Prior Publication Data

US 2018/0192691 A1    Jul. 12, 2018

Related U.S. Application Data

(60) Provisional application No. 62/445,220, filed on Jan. 11, 2017.

(51) Int. Cl.
*A24F 9/02* (2006.01)
*A24F 9/04* (2006.01)
(Continued)

(52) U.S. Cl.
CPC .............. *A24B 13/00* (2013.01); *A24B 15/16* (2013.01); *A24D 1/14* (2013.01); *A24F 9/02* (2013.01);
(Continued)

(58) Field of Classification Search
CPC ...... A24F 3/02; A24F 9/02; A24F 9/04; A24F 1/26; A24F 47/002; A24F 47/004;
(Continued)

(56) References Cited

U.S. PATENT DOCUMENTS 136,487 A * 3/1873 Buynitzky ................ A24F 1/00
                                                    131/180
2,228,951 A * 1/1941 Franklin ................. A24F 13/10
                                                    131/182
(Continued)

FOREIGN PATENT DOCUMENTS

DE          566384 C   * 12/1932   ............... A24F 1/26
DE          676143 C   *  5/1939   ............. A24F 13/02
(Continued)

OTHER PUBLICATIONS

Neusinger, Georg, "Translation of DE 823054", Espacenet.com, Translated Dec. 20, 2019. (Year: 2019).*
(Continued)

*Primary Examiner* — Michael J Felton
*Assistant Examiner* — Sonny V Nguyen
(74) *Attorney, Agent, or Firm* — Smyrski Law Group, A P.C.

(57) ABSTRACT

The invention includes a device for smoking smokeable material. The device has a housing, a rotatable shaft for driving smokeable material towards the first end of the housing as the smokeable material is smoked, at least one radial hole through the shaft for passage of smokeable material from the burning section of the housing into the longitudinal hole of the rotatable shaft.

18 Claims, 9 Drawing Sheets

(51) Int. Cl.
  *A24D 1/14* (2006.01)
  *A24F 13/10* (2006.01)
  *A24B 13/00* (2006.01)
  *A24B 15/16* (2020.01)
  *A61K 31/352* (2006.01)
  *A24F 3/00* (2006.01)

(52) U.S. Cl.
  CPC ............... *A24F 9/04* (2013.01); *A24F 13/10* (2013.01); *A61K 31/352* (2013.01); *A24F 3/00* (2013.01)

(58) Field of Classification Search
  CPC .... A24F 5/10; A24F 5/14; A24F 13/10; A24F 13/02; A24F 13/08; A24F 7/00; A24F 7/02; A24F 7/04; A24D 1/14; A24B 13/00
  USPC ...................... 131/182, 242.5, 190
  See application file for complete search history.

(56) References Cited

U.S. PATENT DOCUMENTS

| | | | | |
|---|---|---|---|---|
| 2,333,896 | A * | 11/1943 | Sonn | A24F 13/02 131/190 |
| 2,832,354 | A * | 4/1958 | Miller | A24F 13/26 131/254 |
| 3,713,451 | A | 1/1973 | Bromberg | |
| 3,993,226 | A * | 11/1976 | Pavenick | A45D 40/04 222/327 |
| 4,252,135 | A * | 2/1981 | Herman | A24F 3/00 131/176 |
| 4,319,587 | A | 3/1982 | Moser | |
| 4,596,258 | A * | 6/1986 | Steiner | A24D 1/00 131/195 |
| 6,172,328 | B1 | 1/2001 | Jones et al. | |
| 6,260,554 | B1 * | 7/2001 | Rowland | A24F 1/26 131/173 |
| 8,869,792 | B1 * | 10/2014 | Lee | A61M 15/06 128/202.21 |
| 8,899,238 | B2 | 12/2014 | Robinson et al. | |
| 8,910,630 | B2 | 12/2014 | Todd | |
| 2004/0217024 | A1 | 11/2004 | Arnarp et al. | |
| 2007/0181140 | A1 | 8/2007 | Xue et al. | |
| 2007/0244436 | A1 * | 10/2007 | Saiki | A61M 5/31528 604/131 |
| 2009/0139532 | A1 | 6/2009 | Ostrom et al. | |
| 2012/0042885 | A1 | 2/2012 | Stone et al. | |
| 2012/0247494 | A1 | 10/2012 | Oglesby et al. | |
| 2013/0014755 | A1 | 1/2013 | Kumar et al. | |
| 2015/0136124 | A1 | 5/2015 | Aronie et al. | |
| 2017/0119039 | A1 | 5/2017 | Dena et al. | |
| 2017/0143039 | A1 * | 5/2017 | Buehler | A24B 15/167 |
| 2017/0188623 | A1 | 7/2017 | Cranford | |
| 2017/0273349 | A1 | 9/2017 | Moore | |

FOREIGN PATENT DOCUMENTS

| | | | | |
|---|---|---|---|---|
| DE | 823054 | C * | 11/1951 | ............ A24F 13/10 |
| FR | 2627674 | A1 * | 9/1989 | ............ A24F 13/08 |
| GB | 236140 | A * | 7/1925 | ......... F16H 61/0295 |
| GB | 524337 | A | 1/1939 | |
| GB | 670198 | A * | 4/1952 | ............ A24F 13/10 |
| WO | 2015175979 | A1 | 11/2015 | |
| WO | 2016122802 | A1 | 11/2016 | |
| WO | 2016187695 | A1 | 12/2016 | |

OTHER PUBLICATIONS

Woiczinski, Herbert, "Machine translation of DE 676143 C", Espacenet.com, Translated May 15, 2020. (Year: 2020).*

Eleonore, Alexis, "Machine translation of FR 2627674 A1," Espacenet.com, Translated Feb. 2, 20201. (Year: 2021).*

Orens et al., Report titled "Marijuana Equivalency in Portion and Dosage," MPG Marijuana Policy Group/University of Colorado Leeds School of Business, Bus. Research Div.; BBC Research & Consulting, v. 12, Aug. 10, 2015, 44 Pages.

Screenshot of 20 x Hollies Fire Logs Eco Heatlogs Wood Briquettes Burner Fuel Heat Firewood, retrieved from eBay on Jan. 12, 2017 at http://www.ebay.co.uk/itm/20×HottiesFireLogsEcoHeatlogsWoodBriquettesBurnerFuelHeatFirewood/ 200908655577.

* cited by examiner

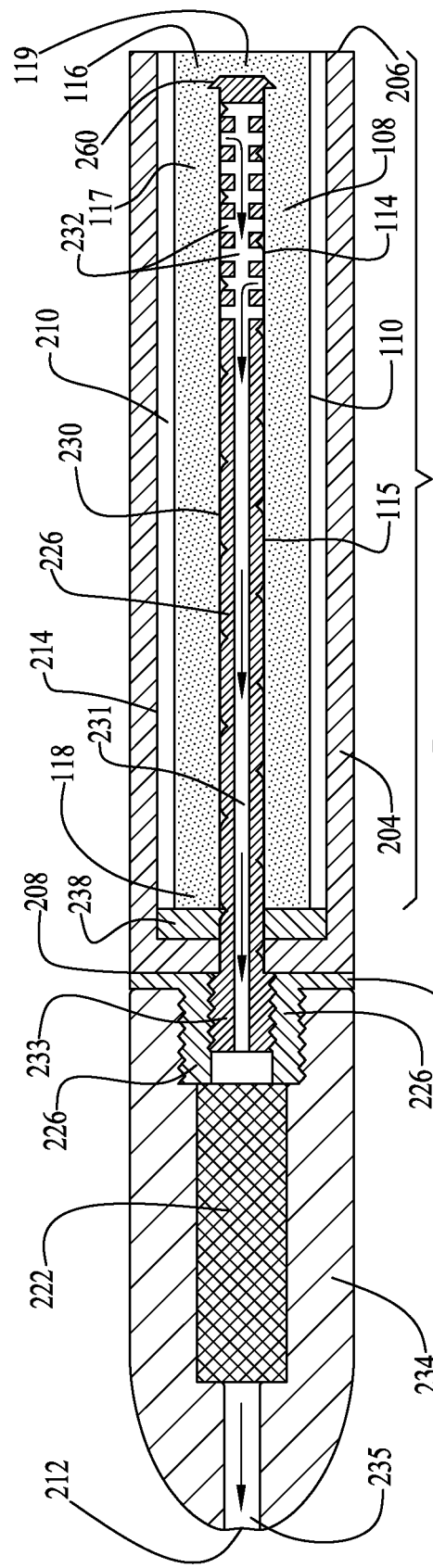

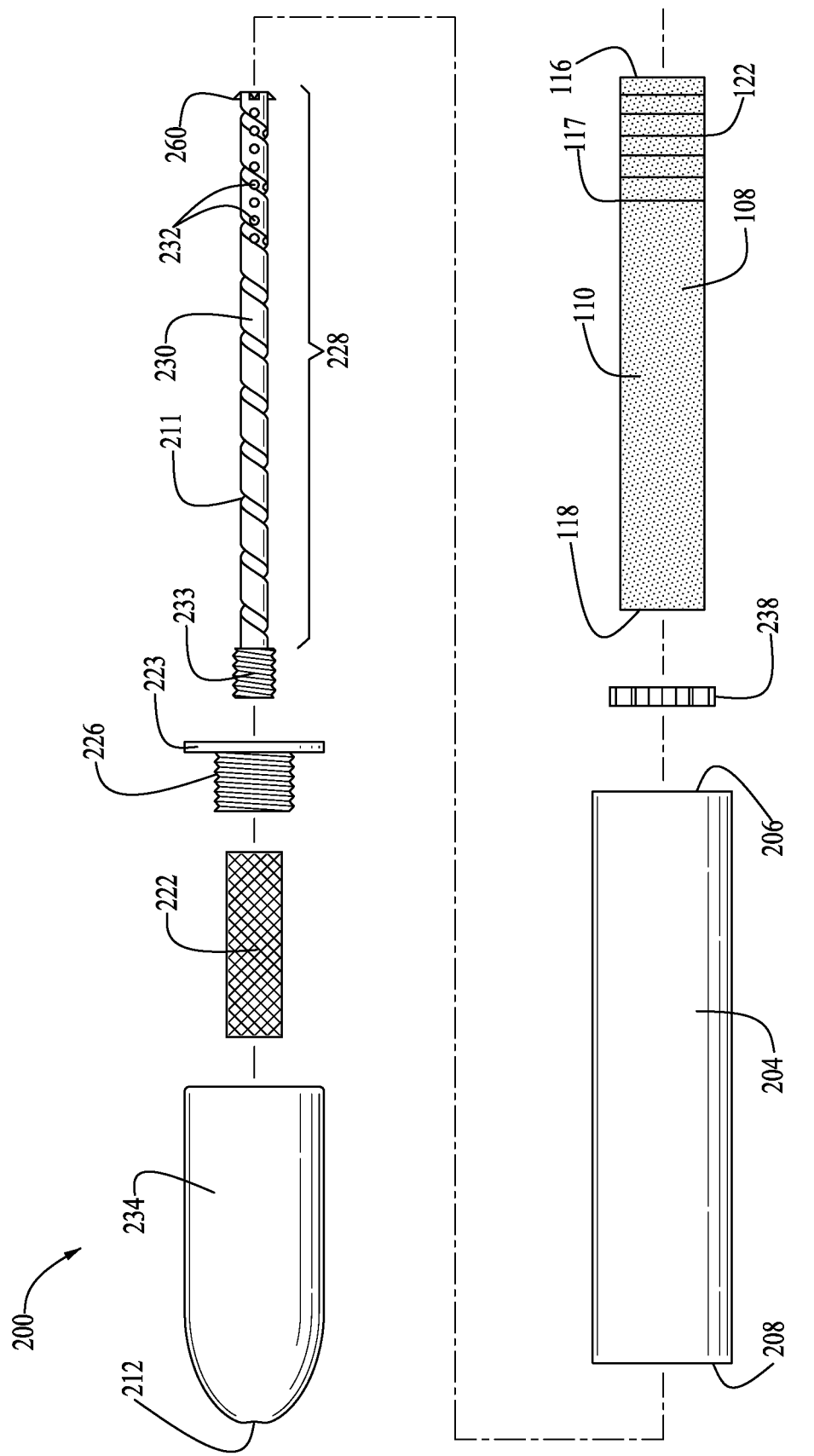

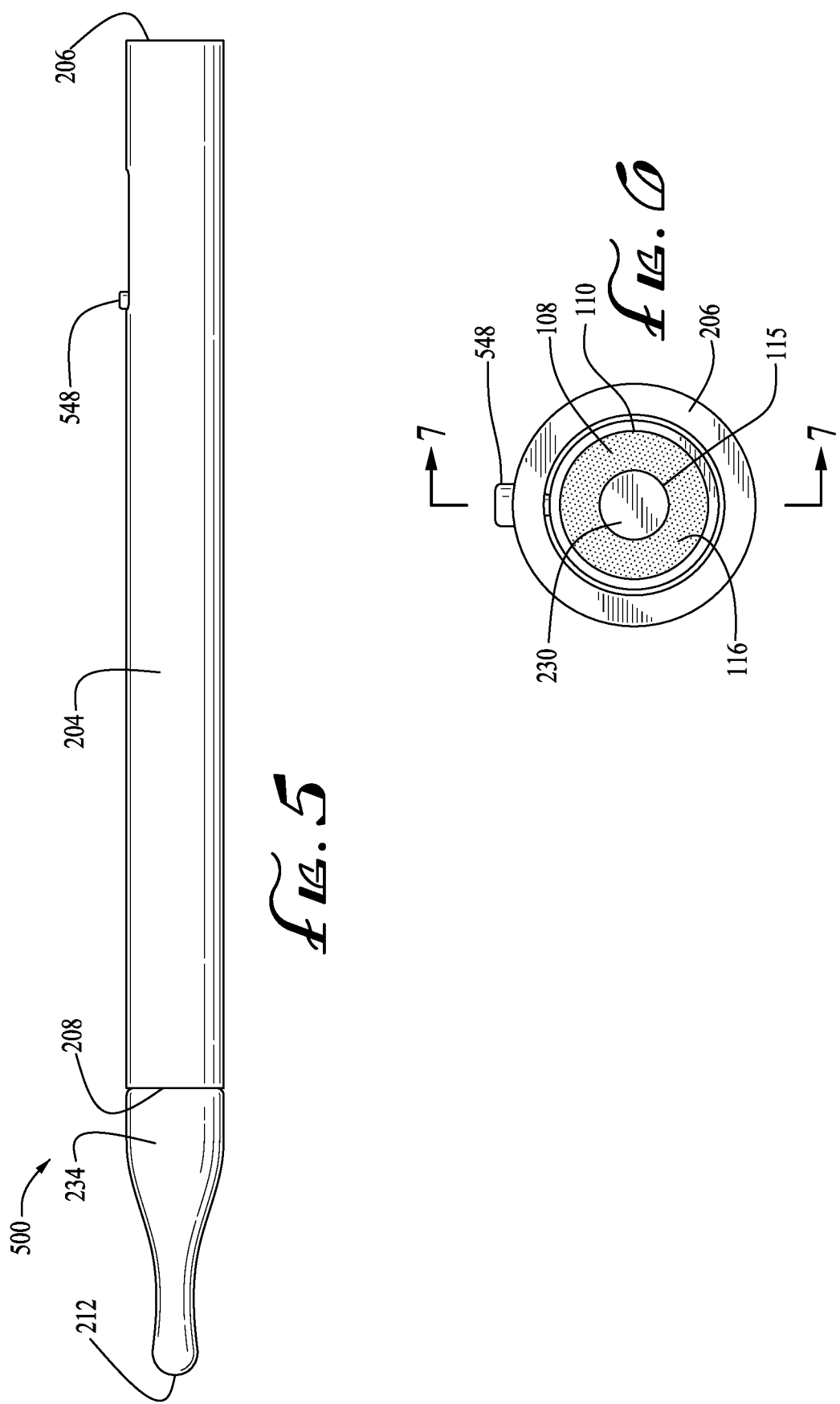

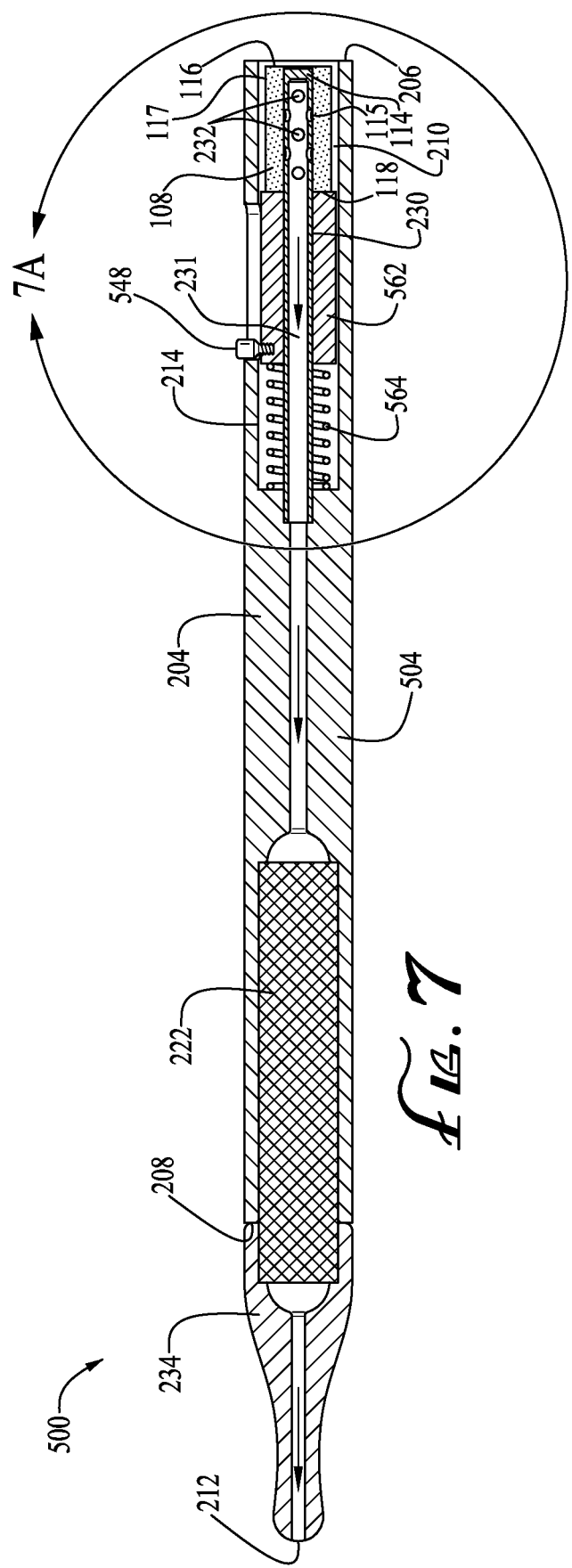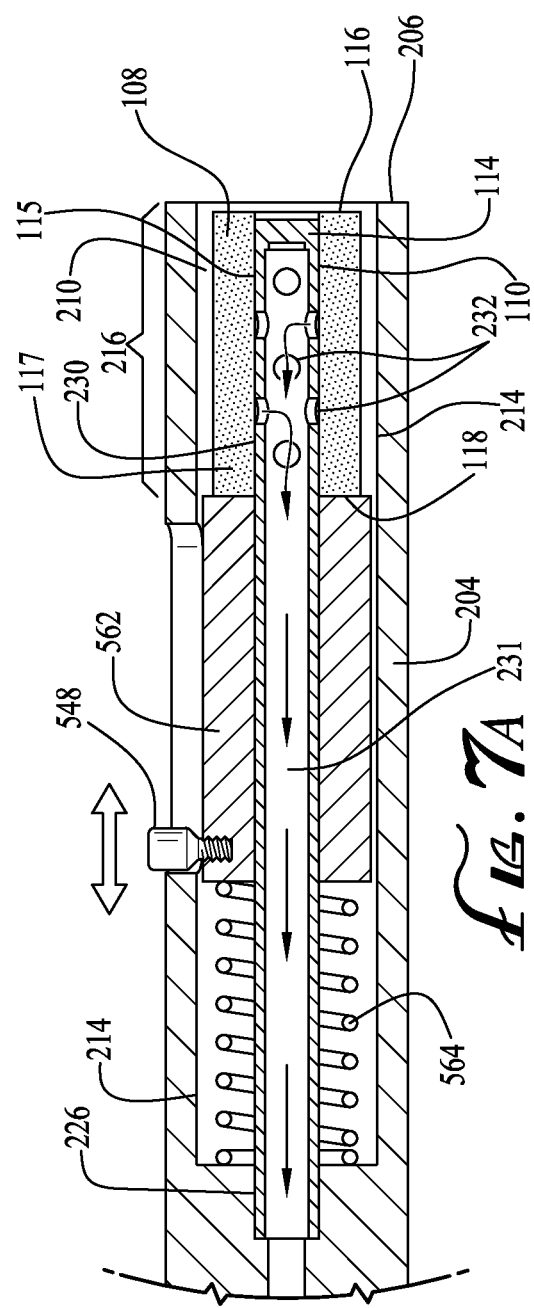

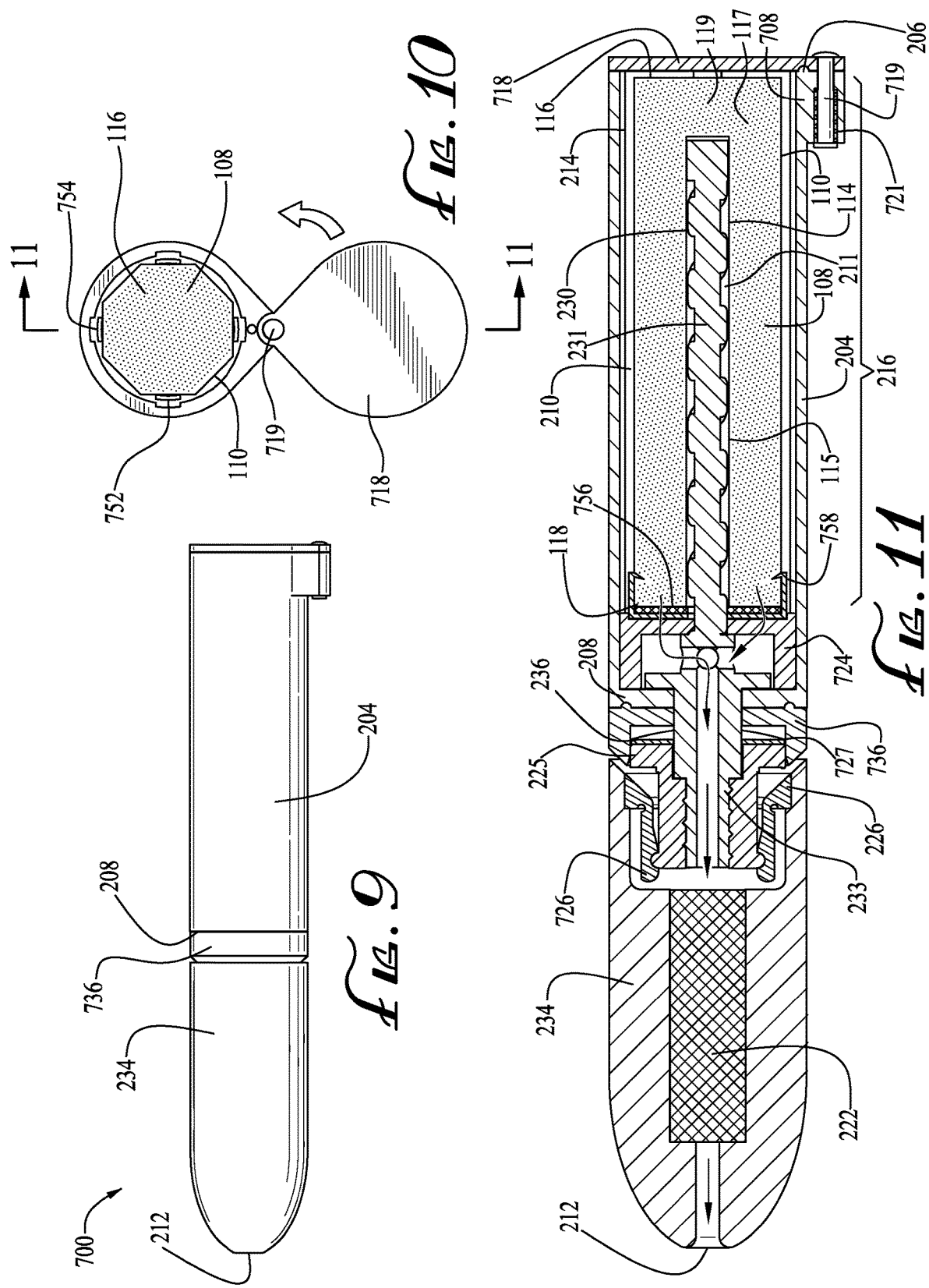

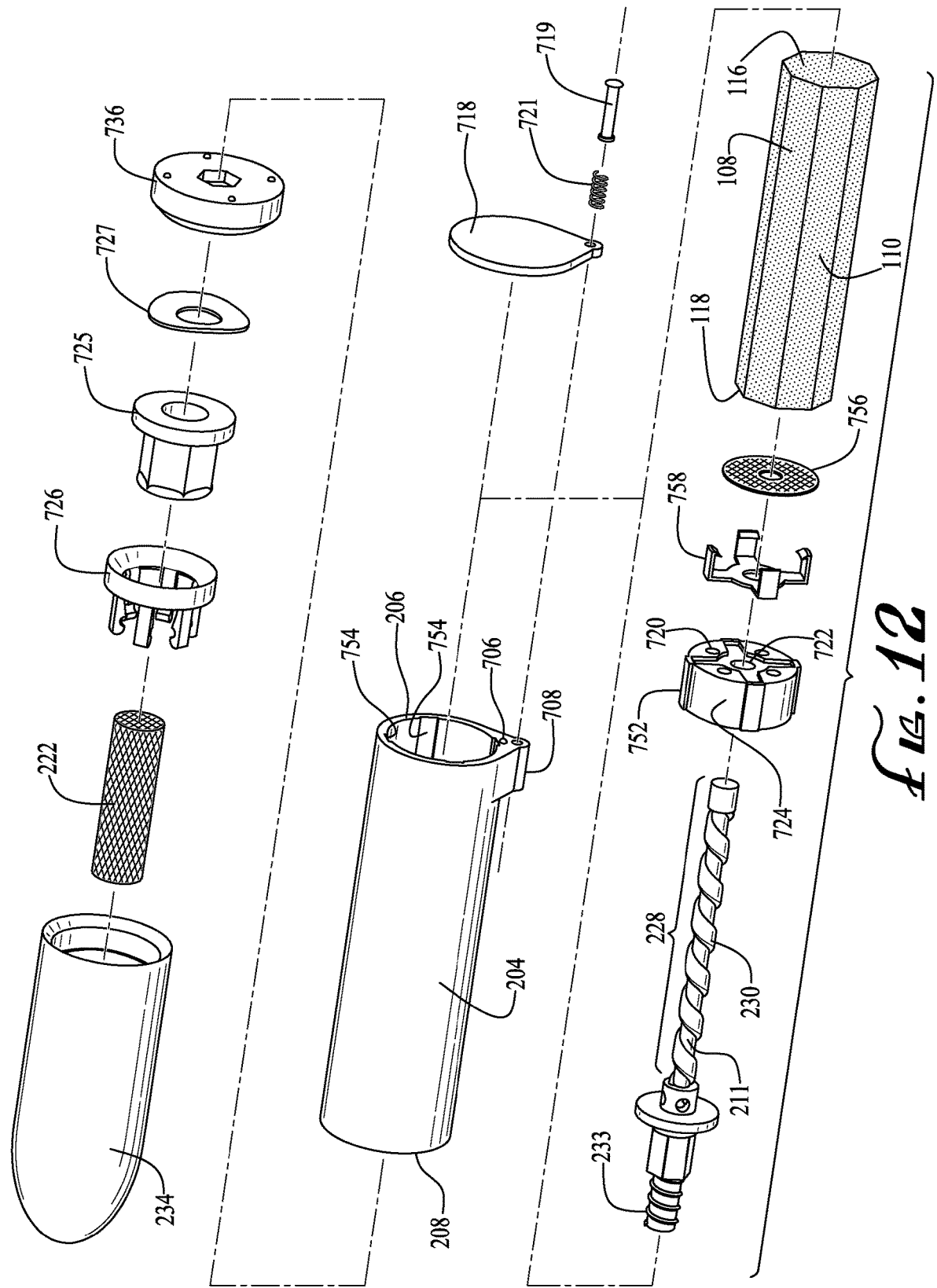

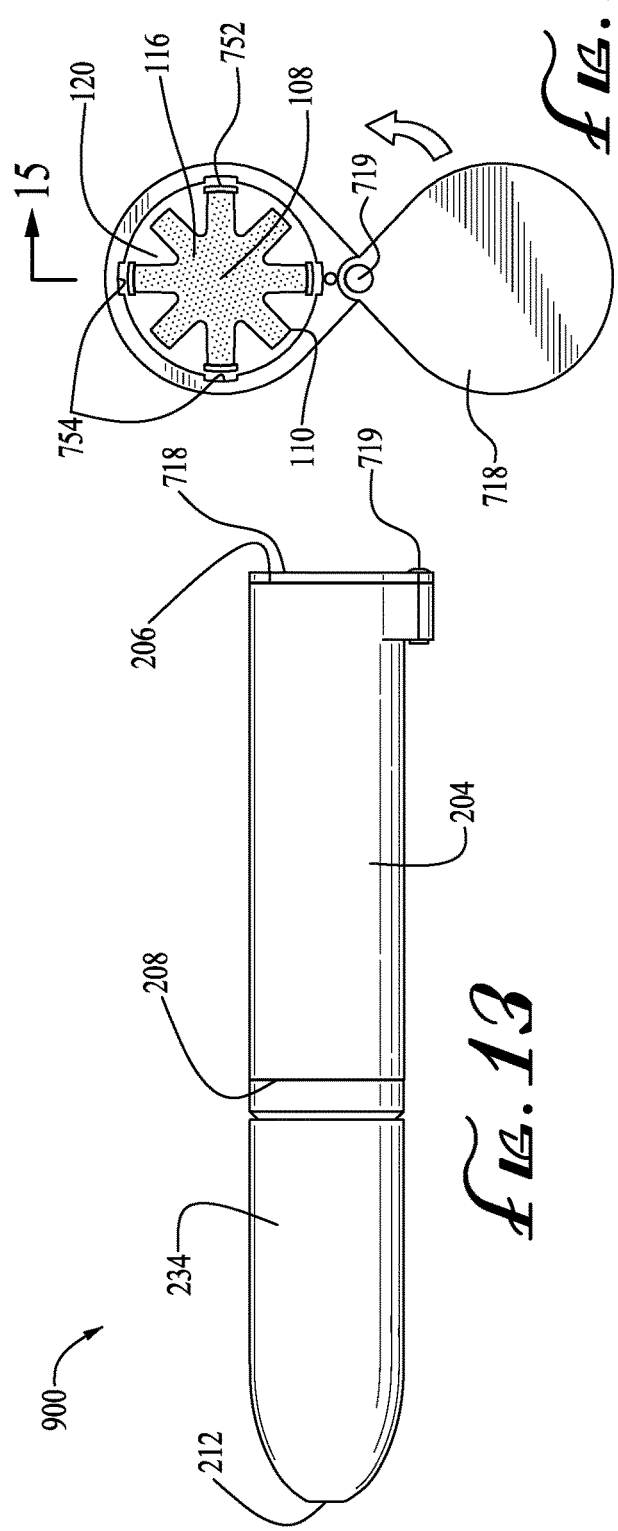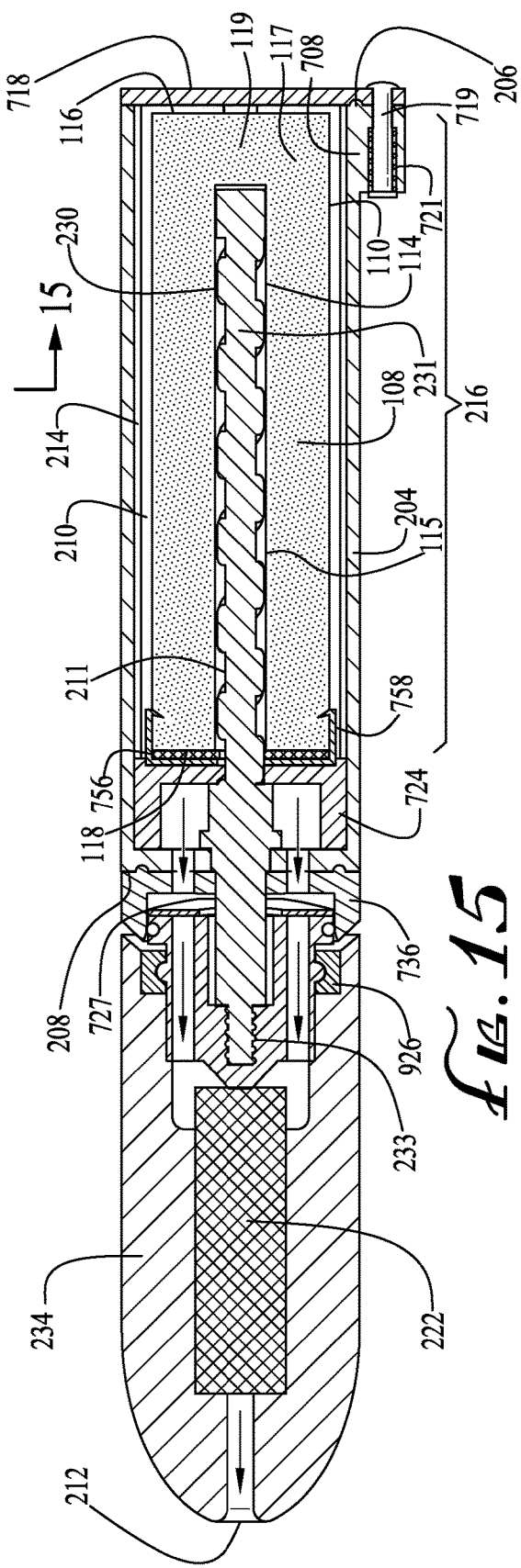

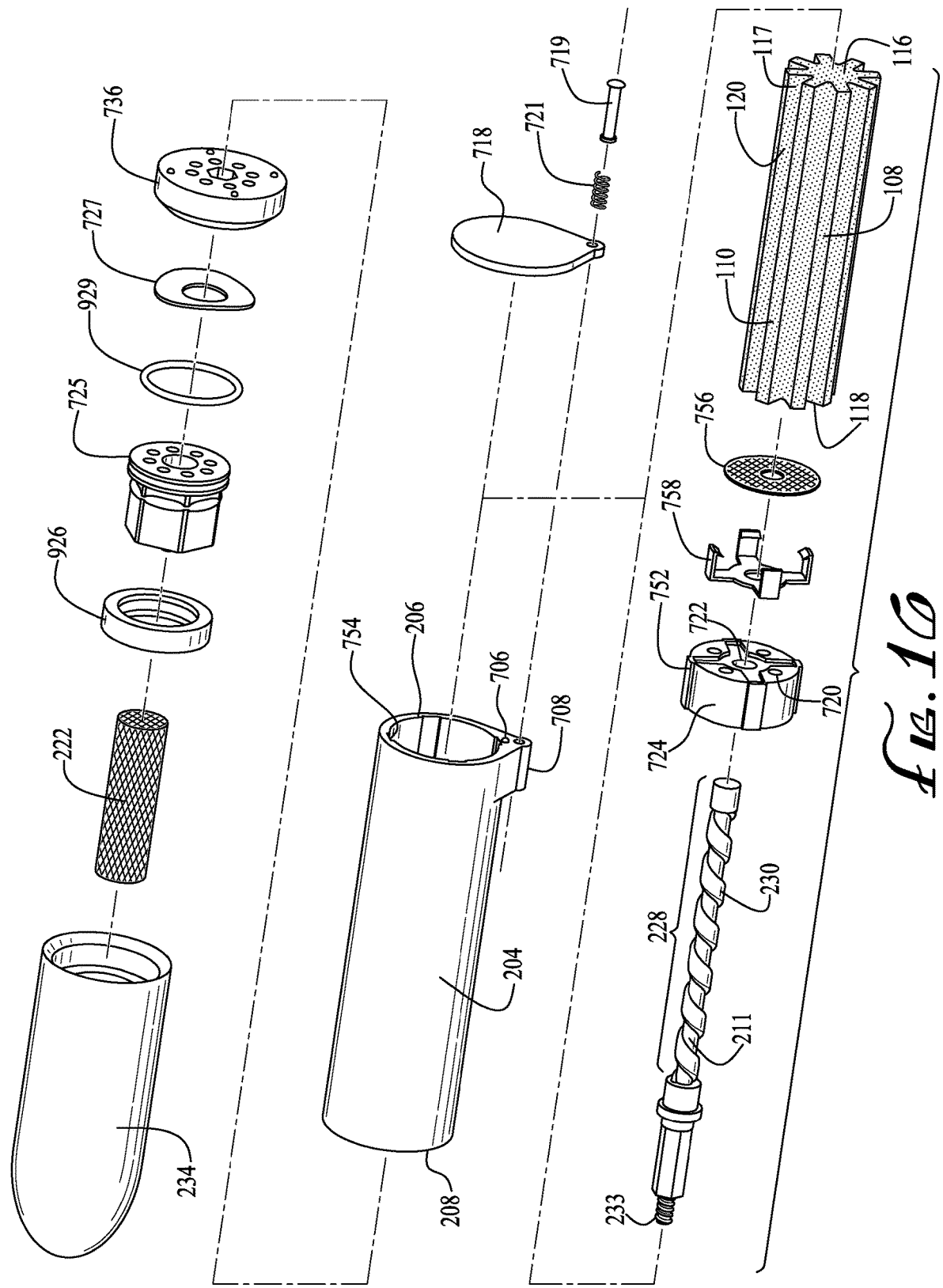

SYSTEM UTILIZING COMPRESSED SMOKABLE PRODUCT

CROSS-REFERENCE TO RELATED APPLICATIONS

The present Application claims the benefit of U.S. Provisional Patent Application No. 62/445,220 titled "COMPRESSED SMOKEABLE PRODUCT AND METHOD OF MAKING, AND PIPE FOR SMOKING COMPRESSED SMOKEABLE PRODUCT," filed Jan. 11, 2017, the contents of which are incorporated herein by reference in their entirety.

BACKGROUND

Smokeable material such as tobacco and marijuana is often stored as a loose product and smoked as a loose product. Devices to smoke loose smokeable material such as pipes and bowls are known. The problem with a user smoking loose product is that it can be messy, cumbersome, and unduly fast-burning. Therefore, there is a need for an improved smokeable product and devices designed for their use to overcome these problems with existing smokeable products.

SUMMARY

The system according to the present invention satisfies this need. The system of the present invention includes a device useful for smoking smokeable material such as a smokeable product, but its use is not limited to the smokeable product of the invention. The device can have a housing having an open first end, a second end, a burning section proximate to the first end, an interior wall, and a longitudinal axis, a receiving region in the burning section for receiving a smokeable material inserted through the open first end of the housing. The device can include a wire mesh filter, which can be replaceable, supported by the interior wall of the housing for filtering impurities from the smoke of the smokeable material. There is a pusher in the housing for pushing the smokeable material through the first end of the housing, advancing the smokeable material and removing ash. A rotatable shaft has an auger section for driving the pusher and extending into the opening of the smokeable material. There can be a longitudinal hole through the rotatable shaft and at least one radial hole through the rotatable shaft for passage of smoke from the smokeable material through the longitudinal hole in the rotatable shaft.

Preferably, there is a mouthpiece at the second end of the housing. The mouthpiece can be rotatable relative to the housing. Smoke passing through the longitudinal hole in the rotatable shaft passes through the mouthpiece. A connector is provided for connecting the mouthpiece to the shaft so that the rotation of the mouthpiece rotates the shaft relative to the housing.

Optionally, there can be a filter in the mouthpiece. Preferably, there is a block preventing smoke from reaching the mouthpiece without passing through the longitudinal hole of the shaft.

Preferably, a portion of the housing is sufficiently transparent or translucent that the smokeable material in the burning section is visible. Optionally, a door sized and shaped for closing the first end of the housing can be provided.

A broadly exemplary device for smoking smokeable material comprises a housing in the first end, second end, burning section proximate to the first end, an inhalation section proximate to the second end, an interior wall, an a longitudinal axis. The first end is open and the burning section is sized and shaped for receiving smokeable material inserted through the first end of the housing. The device includes a rotatable shaft having a longitudinal hole, the shaft adapted for driving the smokeable material towards the second end of the housing. There is at least one radial hole through the shaft for passage of smoke from the burning section of the housing into the longitudinal hole of the rotatable shaft.

In another version of the invention, the device can be provided with a moveable gripper for griping compressed material in the burning section, the gripper being moveable along the longitudinal axis of the housing. The device can include a shaft for driving the smokeable material towards the second end of the housing for having a gripper engage smokeable material in the burning section. The device can include a pusher between the shaft and the gripper, the pusher being moveable along the longitudinal axis of the housing by the shaft.

In another version of the invention, there is a smoke passage control in the housing between the burning section and the inhalation section. The control has one or more longitudinal holes therethrough for passage of smoke from burning the smokeable material in the burning section to the inhalation section. The block prevents smoke from burning the smokeable material passing to the inhalation section without passing through the holes through the control.

The system also includes a method for smoking smokeable material comprising selecting one of the devices described above, placing smokeable material into a burning section, igniting the placed smokeable material, and inhaling smoke from the smokeable material through the mouthpiece.

DRAWINGS

These and other features, aspects, and advantages of the present invention will become better understood with regard to the following description, appended claims, and accompanying drawings where:

FIG. 1 is a side elevation view of a first device having features of the present invention;

FIG. 2 is a front elevation view of the device of FIG. 1;

FIG. 3 is a longitudinal sectional view of the device of FIG. 1 taken on line 3-3 in FIG. 2;

FIG. 4 is an exploded side elevation view of the device of FIG. 1;

FIG. 5 is a side elevation view of a second device having features of the present invention;

FIG. 6 is a front elevation view of the device of FIG. 5;

FIG. 7 is a longitudinal sectional view of the device of FIG. 5 taken on line 7-7 in FIG. 6;

FIG. 7A is a longitudinal sectional view of a portion of the device of FIG. 5 taken in area 7A in FIG. 7;

FIG. 9 is a side elevation view of a third device having features of the present invention;

FIG. 10 is a front elevation view of the device of FIG. 9 with a door in an open position;

FIG. 11 is a longitudinal sectional view of the device of FIG. 9 taken on line 11-11 in FIG. 10 with the door closed;

FIG. 12 is an exploded perspective view of the device of FIG. 9;

FIG. 13 is a side elevation view of a fourth device having features of the present invention;

FIG. 14 is a front elevation view of the device of FIG. 13;

FIG. 15 is a longitudinal sectional view of the device of FIG. 13 taken on line 15-15 in FIG. 14; and FIG. 16 is an exploded perspective view of the device of FIG. 13.

DESCRIPTION

Figure 8:
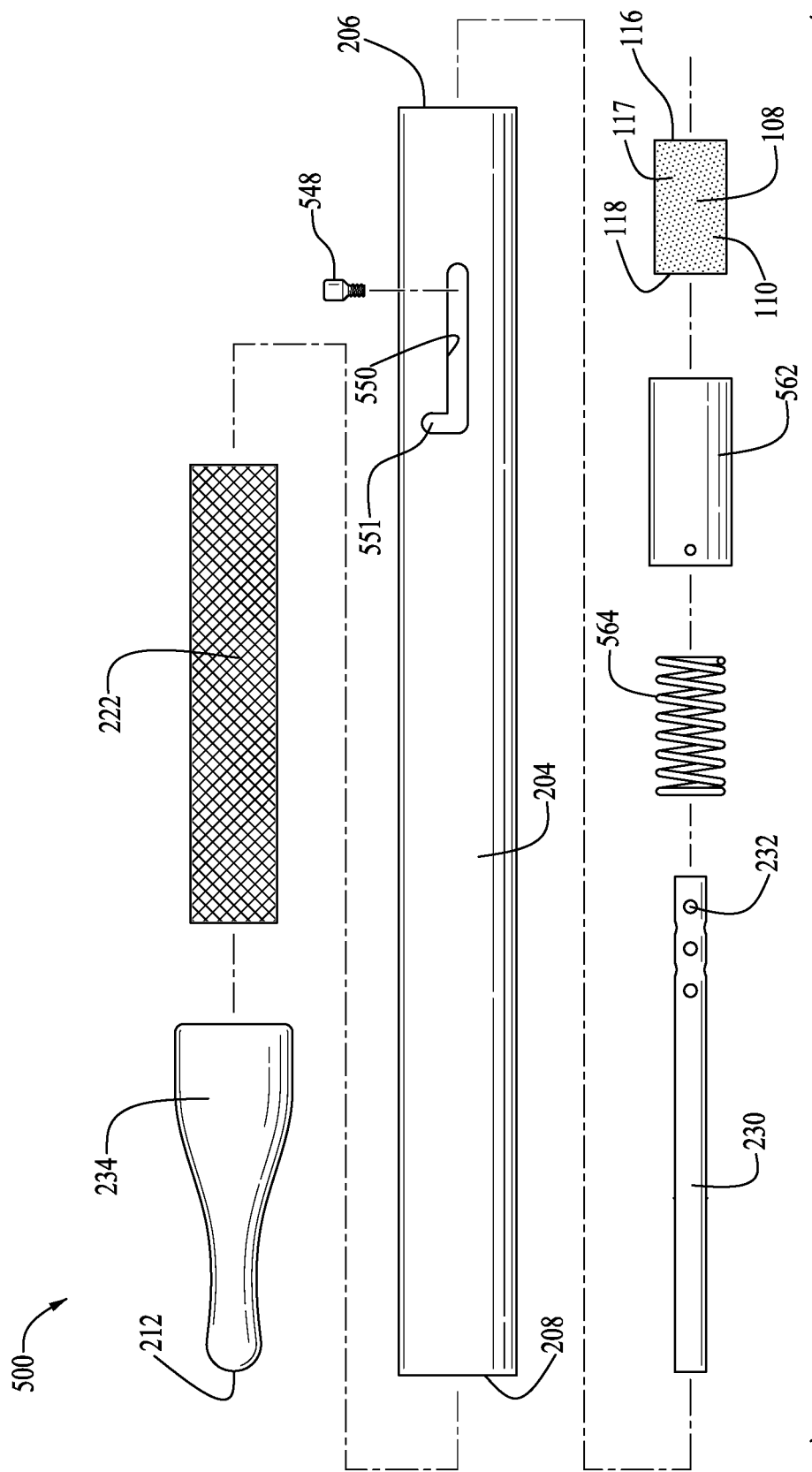
FIG. 8 is an exploded side elevation view of the device of FIG. 5.

In general, with regard to FIGS. 1-16, the present invention comprises compressed smokeable product 108 and devices 200 useful for smoking the compressed smokeable product 108 or other smokeable product. The present invention solves the problems of smoking loose smokeable material by compressing the smokeable material into the smokeable product 108. The compressed smokeable product 108 can be heated until it burns, and because of the compression the rate of burning can be limited or the burning can be stopped so that the smokeable material 108 is not wasted. The compressed smokeable product 108 is prepared for smoking so that the consumer does not need to prepare the compressed smokeable product 108 prior to use, making the smokeable product easier to use. Compression of the smokeable product is also advantageous in that compression prevents the smokeable material from drying out quickly. An additional benefit is that there is more pressure across the compressed smokeable product 108 so that when the user draws air through the compressed smokeable material, less air and more of the smokeable material is inhaled by the user. This allows the user to take a smoother inhalation with less lung expansion.

As used herein, the following terms and variations thereof have the meanings given below, unless a different meaning is clearly intended by the context in which such term is used.

The terms "a," "an," and "the" and similar referents used herein are to be construed to cover both the singular and the plural unless their usage in context indicates otherwise.

As used herein, the term "comprise" and variations of the term, such as "comprising" and "comprises," are not intended to exclude other components.

The term "device" refers to any apparatus that can be used to smoke compressed smokeable material. Exemplary devices include pipes, electronic pipes, vaping devices, bongs, and bowls.

As used herein, "smokeable material" can be any material that is able to be smoked such as, for example, a plant such as tobacco, marijuana, herbs, or a medicinal substance. Smokeable material can also be concentrated tetrahydrocannabinol (THC or cannabinoids) such as THC wax or other solid forms of THC or a medicinal compound. The smokeable material can be substantially pure, or it can contain material such as stems or seeds that can be smoked even if not removed, and can include additives such as preservatives and colorants.

"Feed" smokeable material refers to starting material that is used to make a compressed smokeable material product. Feed smokeable material can contain a large portion of smokeable material, and can also contain seeds and stems. Feed smokeable material can be material that is left over from the preparation of other products such as cigarettes.

As used herein, smokeable material that is compressed is referred to as a "compressed smokeable product," "nugget," or "log." The compressed smokeable product can be smoked in any device such as a pipe or a bowl. The compressed smokeable product can be smoked in a device, such as a pipe, that is sized to fit the shape of the nugget, as described further below. Oils, flavors, cannabis concentrates, caffeine, and other burnable herbs may be added to the compressed smokeable product, either before or after the smokeable material is compressed, or while the smokeable material is compressed.

As used herein, the term "density test" means the percentage of compression of the compressed smokeable product. The density of an object is the mass per unit volume, and is conventionally expressed as grams per cubic centimeter (g/cm$^3$). To perform the density test, the density of the smokeable material is first measured. The smokeable material is compressed into the compressed smokeable product, after which the density of the compressed smokeable product is measured. The density of the smokeable material is then compared to the density of the compressed smokeable product, resulting in a percentage increase. For example, the compressed smokeable product can be compressed 20% to 150% as compared to the starting smokeable material.

As used herein, the "diameter" of an irregularly shaped object is the object's equivalent spherical diameter.

The invention provides for a product made of smokeable material which can be compressed and formed into a compressed smokeable product 108, shown in FIGS. 2-4, 6-8, 10-12, and 14-16. The compressed smokeable product 108 can be any shape, such as, for example, an elongated cylinder having a first end 116, a second end 118, and an outer surface 110. The vertical cross-section of the compressed smokeable product 108 can be any shape, such as, for example, circular, polygonal, or star-shaped.

The compressed smokeable product 108 can be made out of any part of a plant, such as, for example, the bud, the stalk, the leaves, the stems, and the roots of plant starting material. Alternatively, the compressed smokeable product 108 can be made with less desirable looking material, such as small pieces of cannabis flower that break off of larger buds as the result of regular handling or that is trimmed off the bud in order to beautify it; the small pieces are commonly called "shake."

As shown in FIGS. 3, 4, 7, 11, 12, 15 and 16, the compressed smokeable product 108 has a first end 116 having a burning section 117, and a second end 118 opposed to the first end 116. The compressed smokeable product 108 can have a length of from about 4 to about 50 millimeters, and a diameter from about 5 to 15 millimeters.

In one embodiment, there is a longitudinally extending opening 114 through the product 108, the longitudinally extending opening 114 being parallel with, and preferably coincident with the central longitudinal axis of the compressed smokeable product 108. The longitudinally extending opening 114 provides an inner surface 115. The longitudinally extending opening 114 may extend totally or partially through the center or substantially the center of the compressed smokeable product 108. The longitudinally extending opening 114 can be any shape in vertical cross section, such as, for example, circular, elliptical, polygonal, spiral, or zig-zag. The longitudinally extending opening 114 can extend completely through the center of the compressed smokeable product 108, as shown in FIGS. 6 and 7. Alternatively, the longitudinally extending opening 114 extends only partially through the center of the compressed smokeable product 108, with the longitudinally extending opening 114 extending to the second end 118 but not the first end 116, leaving a solid portion 119 between the end of the longitudinally extending opening 114 and the first end 116, as shown in FIGS. 3, 11, and 15.

In another embodiment, the compressed smokeable product 108 can have one or more grooves 120 partially or completely along the outer surface 110 of the compressed smokeable product 108, as shown in FIGS. 14-16. The grooves 120 can be from about 1 millimeter to about 6 millimeters deep.

The compressed smokeable product 108 can contain a predetermined concentration or amount of THC or other medicament and can be prescribed by a medical practitioner. THC can be measured by any means known in the art. For example, the concentration of THC can be measured in a sample and expressed as a percentage or grams of THC per grams of plant material. Commercially available instruments such as, for example, the CannaDx™ (MyDX, Inc., San Diego, Calif.) sensor can measure the concentration of THC in a compressed smokeable product.

The amount, or dose, of THC per gram compressed smokeable product is variable, and depends upon the concentration of the THC in the compressed smokeable product. (See e.g. Orens et al., Marijuana Equivalency in Portion and Dosage, 2015.) The compressed smokeable product 108 can contain a THC content of from about 5 to about 50% by weight.

As shown in FIG. 4, the compressed smokeable product 108 can also have longitudinally spaced apart indicia 122 such as a notch or other markings such as ink on the outer surface 110 to indicate a dose of medicament, such as THC, that can be obtained by a user by smoking the compressed smokeable product 108 between each indicia 122. Alternatively, the amount of medicament consumed by the user can be measured per inhalation.

Preferably the compressed smokeable product 108 is sized to fit one or more of the devices disclosed herein that can be used to smoke the compressed smokeable product 108. Alternatively, the compressed smokeable product 108 can be smoked in other pipes, a vape device, a bowl, or other burning units.

The invention also contains a kit for smoking. The kit comprises a container and one or more compressed smokeable products 108 in the container. Each compressed smokeable product 108 has smokeable material compressed by at least 20% measured by the density test and in the form of an elongated cylinder. The kit can have a label on the container containing dosage information. Dosage information can include, for example, the amount of THC per inhalation. Preferably each individual product in the container is of substantially the same size and has substantially the same THC content if the smokeable material is marijuana.

The compressed smokeable product 108 can be formed by compression of ground starting smokeable material in a mold. An inert, or chemically inactive binding material, such as, for example, starch or oil such as coconut oil or avocado oil, can be used to hold the ground smokeable material together. In another embodiment, the compressed smokeable product 108 is formed by the application of pressure with or without heat, and optionally the addition of binding material. For example, the feed material can be subjected to a pressure of about 2 to about 20 psig. In another embodiment, the compressed smokeable product 108 is formed by the application of steam and pressure and optionally the addition of binding material.

The density of the compressed smokeable product 108 preferably is, at a minimum, increased at least about 20% as compared to the starting smokeable material before compression. The maximum density of the compressed smokeable product is around 150% as compared to the starting smokeable material before compression. Preferably, the density of the compressed smokeable product is from around 30 to 40% greater than the density of the starting smokeable material before compression.

The longitudinally extending opening 114 can be formed in the compressed smokeable product 108 while forming the compressed smokeable product 108, such as by molding or extruding, or after forming the compressed smokeable product 108, such as by drilling mechanically or with a laser.

The present invention also includes the device 200 that can be used with the compressed smokeable product 108. The device 200 preferably is portable and may be disposable. FIGS. 1-4 depict one version of a device 200 useful to smoke the compressed smokeable product 108. The device 200 includes an elongated linear housing 204 that is substantially cylindrical, with an interior wall 214 and a longitudinal axis. The housing 204 can be made out of any rigid material such as, for example, metal, glass, wood, or plastic. In one aspect, part or all of the housing 204 is translucent or transparent such that the compressed smokeable product 108 in the housing 204 is visible. The housing 204 can be from about 20 millimeters to about 100 millimeters in length and from about 5 millimeters to about 20 millimeters in diameter.

The housing 204 has an open first end 206 and a second end 208 which is distal to the first end 206, with a mouthpiece 234 proximate to the second end 208. The housing 204 has a receiving region 216 proximate to the first end 206 for receiving a smokeable product such as, for example, the compressed smokeable product 108 described herein. Inside the receiving region 216, and proximate to the first end 206, is a burning section 210. The burning section 210 is an area in which the smokeable product is ignited or combusted. The compressed smokeable product 108 of the invention can be sized to fit within the receiving region 216. The longitudinally extending opening 114 can be placed on an elongated hollow shaft 230, as shown in FIGS. 3, 7, 7A, 11, and 15. The first end 206 can be configured to receive one of a variety of different corresponding designs of compressed smokeable product 108 in a lock and key configuration, in which only a smokeable product with the specific shape and/or size that is complementary to the device can fit into the device.

The shaft 230 can have an auger section 228 with a groove 211 such as a worm gear groove that extends longitudinally through the housing 204, and a threaded end 233 that is proximal to the second end 208 of the housing 204. The shaft 230 can contain one or more openings 232 in the burning section 210, such as radial holes, that can allow the passage of smoke from the combusted compressed smokeable product 108 through the opening 232, then through a longitudinal hole 231 in the center of the shaft 230, and finally to an inhalation section 212, as indicated by the arrows in FIGS. 3, 7 and 7A. The shaft 230 can be made out of a rigid material such as, for example, metal or plastic. The shaft 230 can have means for retaining the smokeable product within the housing, such as, for example, barbs 260 at the end of the shaft 230 proximate to the first end 206 of the housing 204.

The device 200 can have a mouthpiece 234 proximal to the second end 208 of the housing 204. The mouthpiece 234 is positioned to receive smoke passing through the longitudinal hole 231 of the shaft 230 and has a longitudinal opening 235 therethrough. The mouthpiece 234 can be removably connected to the housing 204 such as by a compression fit or by threading onto a correspondingly threaded mouthpiece connector 226, which is connected to the shaft 230 by screwing on to the threaded end 233 of the shaft 230. The connector 226 has a flange 223 butted against the second end 208 of the housing 204. The connector 226 has a longitudinal hole therethrough for passage of smoke from the longitudinal hole 231 of the shaft 230 for transmission to the user through the mouthpiece 234. Rotation of the connector 226 by rotation of the mouthpiece 234 causes the shaft 230 to rotate which moves the pusher 238 along the auger section 228 of the shaft 230 for longitudinally moving the smokeable product into and out of the receiving region 216. As the smokeable product is spent, the user can advance more material forward into the burning section 210. The pusher 238 also helps prevent smoke from reaching the longitudinal opening 235 in the mouthpiece 234 without passing through the longitudinal hole 231 of the shaft 230.

There can be a filter 222 in the mouthpiece 234 for filtering impurities in the smoke from the smokeable material. The filter can be made from any material that can remove impurities. Exemplary material can be cellulose acetate fiber, paper or activated charcoal. The filter 222 can be removable and replaceable by turning the mouthpiece 234 in relation to the mouthpiece connector 226 until the mouthpiece 234 separates from the mouthpiece connector 226.

With reference to the other versions of a smoking device, the same reference numbers are used for components that are the same or substantially the same.

With reference to the device 500 shown in FIGS. 5-8, a second version of the device 500 has an annular slip lock 562 within and concentric with the housing 204, and mounted over the shaft 230, as shown in FIGS. 7-8. The slip lock 562 is biased towards the burning section 210 with biasing means such as, for example, a coil spring 564 concentric with and mounted on the shaft 230. One end of the spring 564 pushes against the slip lock 562 and the other against a solid body plug 504 within the housing 204, which can be made part of the housing 204 or can be a separate component placed within the housing 204. The slip lock 562 ejects the combusted or partially combusted compressed smokeable product 108 out of the first end 206 of the housing 204. The slip lock 562 can be locked or released by means of a slip lock pin 548 located on the outside of the housing 204. The slip lock pin 548 can move longitudinally in a slip lock pin path 550 that extends through the housing 204 and can be locked into a notch 551 extending circumferentially from the pin path 550, to retain the smokeable material in the housing, or moved out of the notch 551 and along the slip lock pin path 550 to eject the combusted or partially combusted compressed smokeable product 108 out of the housing first end 206. In FIGS. 7 and 7A, the slip lock pin 548 is shown in its closed and locked position, which prevents coil spring 564 from ejecting the compressed smokeable product 108. The mouthpiece 234 is connected to the housing 204 by, for example, snap fitting. The filter 222 can be changed by the user disassembling the mouthpiece 234 from the housing 204, removing the used filter 222 and inserting a new filter 222 into the housing 204.

With reference to a third and fourth version of the device (700 and 900) shown in FIGS. 9-12 and FIGS. 13-16, respectively, smoke does not flow down the longitudinal hole 231 of the shaft 230. Instead, a cylindrical pusher 724 with axial smoke holes 720 therethrough is mounted on the shaft 230 with the shaft 230 passing through a central opening 722 in the cylindrical pusher 724, as shown in FIGS. 11 and 15. Smoke passes through the axial holes 720 of the pusher 724 as shown by the arrows in FIGS. 11 and 15. The pusher 724 can be made out of any rigid material such as plastic or metal. The pusher 724 can move longitudinally along the shaft 230 to either advance or retract the compressed smokeable product 108 within the burning section 210. The auger section 228 of the shaft 230 drives the pusher 724. For example, the auger section 228 can have a worm gear groove 211 along the longitudinal axis, and the pusher 724, mounted on the shaft 230 with central opening 722, can slide in the groove 211 as the shaft 230 rotates, allowing the compressed smokeable product 108 to advance or retract within the housing 204. The pusher 724 can also be used to push combusted smokeable product and ash out through the first end 206 of the housing 204. The pusher 724 can be fitted so that it is retained within the housing 204. In one aspect, the pusher 724 can have protrusions 752 on the periphery that fit into channels 754 that extend substantially through the interior wall 214 of the housing 204 but do not extend to the opening in the first end 206 of the housing 204. The pusher 724 slides along the inside of the housing 204 with the protrusions 752 in the channels 754 but remains retained in the housing 204.

The device 700 can also have a gripper 758 proximate to the pusher 724 that has means such as claws to grip the compressed smokeable product 108 and retain it within the burning section 210, as shown in FIGS. 11, 12, 15 and 16. There can be a screen 756, such as a wire mesh screen, which sits inside the gripper 758 for filtering large particles of combusted smokeable product. The screen 756 can be replaceable. Both the gripper 758 and the screen 756 are mounted on the shaft 230.

The device 700 can have a door 718 mounted on the housing 204 that is sized and shaped for substantially closing the first end 206. The door 718 can have an open position for inserting the compressed smokeable product 108 into the housing 204 and a closed position for retaining the compressed smokeable product 108 in the housing 204 for storage. The door 718 can be totally removable, or as shown in FIGS. 9-11 and 13-15, can be hinged on a pin 719 biased with a spring 721, where the pin 719 and the spring 721 are in a corresponding opening 706 extending through a protrusion 708 on the housing 204. The door 718 can be held in the closed position such as by a loose compression fit, a friction fit closure, or fastening means such a loop and hook fasteners such as Velcro®.

There is a rotatable section 736 between the housing 204 and the mouthpiece 234. The rotatable section 736 fits onto the housing connector 225 portion of the shaft 230. Rotation of the rotatable section 736 rotates the shaft 230 and moves the pusher 724 along the grooves 211 of the shaft 230, thus moving the compressed smokeable product 108 in or out of the burning section 210. Rotation of the shaft 230 towards the first end 206 results in unburnt compressed smokeable product 108 being advanced to the first end 206 of the housing 204 and burnt or combusted compressed smokeable product 108 being expelled from the housing 204. Rotation of the rotatable section 736 towards the second end 208 of the housing 204 results in the compressed smokeable product 108 being retained in the housing 204.

As shown in FIGS. 11 and 12, there can be a housing connector 725 that fits into a gripping mouthpiece connector 726. The housing connector 725 connects the mouthpiece 234 to the rotatable section 736. The gripping mouthpiece connector 726 holds the filter 222 with gripping means such as claws. Alternatively, the housing connector 725 can fit into an annular mouthpiece connector 926 as shown in FIG. 16. Also shown in FIG. 16, there can be a spring washer 727 between the housing connector 725 and the rotatable section 736. The spring washer 727 applies constant force on the housing connector 225 and rotatable section 736. Optionally, there can be an O-ring 929 between the spring washer 727 and housing connector 725 as shown in FIG. 16. The O-ring 929 provides a seal to prevent the smoke from not going through the filter 222.

In use, the user places a compressed smokeable product 108 into the open first end 206 of the device 200, 500, 700, 900 while aligning the longitudinally extending opening 114 on the shaft 230. The user then lights the first end of the compressed smokeable product 108 with a match or lighter, which ignites the compressed smokeable product 108 in the burning section 210. The user then places the mouthpiece 234 in his mouth, and inhales the combusted smokeable product 108 through the inhalation section 212. The user can advance the compressed smokeable product 108 in the burning section 210 by rotation of the rotatable section 236 and/or mouthpiece 234 which rotates the pusher 724, thus pushing unsmoked smokeable product towards the open first end 206 and expelling used smokeable product out the open first end 206. The used smokeable product can be scraped or cut off of the compressed smokeable product 108. If the user desires, he can smoke all or part of the compressed smokeable product 108, or can smoke the compressed smokeable product 108 between two or more indicia 122. If only part of the smokeable product is smoked, the user can move the door 718 to the closed position and store the remainder of the compressed smokeable product 108 for later use.

There are several advantages of using a lock/key type compressed smokeable product 108 and device 200, 500, 700, 900. For example, one advantage is that the compressed smokeable product 108 can be loaded very quickly into the device 200, 500, 700, 900 since the shape of the compressed smokeable product 108 fits into the shaft 230 within the burning section 210 of the device 200.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure.

What is claimed is:

1. A device for smoking smokable material comprising:
   a housing having a first end, a second end, a burning section proximate to the first end, and a longitudinal axis;
   a rotatable shaft having a worm gear spiral groove with an axial hole and a plurality of parallel radial holes passing through and perpendicular to the axial hole formed therein;
   a pusher in the housing for pushing the smokable material toward the first end of the housing and toward the plurality of parallel radial holes, the pusher encircling and contacting the rotatable shaft and being movable along the longitudinal axis of the housing by the rotatable shaft;
   a mouthpiece formed separately from the housing and positioned at the second end of the housing; and
   a connector for connecting the mouthpiece to the rotatable shaft;
   wherein the connector is configured to receive a threaded end of the rotatable shaft such that rotation of the mouthpiece in a first direction causes rotation of the connector and the rotatable shaft in the first direction, causing the rotatable shaft to move the pusher and the smokable material within the housing along the longitudinal axis toward the first end, and rotation of the mouthpiece in a second direction causes rotation of the connector and the rotatable shaft in the second direction, causing the rotatable shaft to move the pusher within the housing along the longitudinal axis away from the first end;
   wherein combustion of the smokable material positioned around the rotatable shaft and inhalation from the mouthpiece causes smoke produced from the smokable material to pass through the plurality of parallel holes into the axial hole and to the mouthpiece.

2. The device of claim 1 wherein at least a portion of the housing is sufficiently transparent or translucent that smokable material in the burning section is visible.

3. The device of claim 1 wherein the smokable material is in the burning section.

4. The device of claim 1 further comprising a barb formed at a remote end of the rotatable shaft.

5. A device for smoking smokable material comprising:
   a housing having a first end, a second end, a burning section proximate to the first end, an inhalation section proximate to the second end, and a longitudinal axis, wherein the first end is open, and wherein the burning section is sized and shaped for receiving smokable material inserted through the first end of the housing;
   a rotatable shaft having a worm gear spiral groove with an axial hole and a plurality of parallel radial holes passing through and perpendicular to the axial hole formed therein, the rotatable shaft adapted for driving the smokable material toward the first end of the housing and toward the plurality of parallel radial holes;
   a pusher located within the housing and encircling and engaging the rotatable shaft;
   a mouthpiece formed separately from the housing, positioned adjacent to the housing, and positioned to receive smoke; and
   a connector configured to receive a threaded end of the rotatable shaft such that rotation of the mouthpiece in a first direction causes rotation of the connector and the rotatable shaft in the first direction, causing the rotatable shaft to move the pusher and the smokable material in the housing along the longitudinal axis toward the first end, and rotation of the mouthpiece in a second direction causes rotation of the connector and the rotatable shaft in the second direction, causing the rotatable shaft to move the pusher in the housing along the longitudinal axis away from the first end;
   wherein combustion of the smokable material positioned around the rotatable shaft and inhalation from the mouthpiece causes smoke produced from the smokable material to pass through the plurality of parallel holes into the axial hole and to the mouthpiece.

6. The device of claim 5 further comprising a barb formed at a remote end of the rotatable shaft.

7. The device of claim 6 further comprising a filter in the mouthpiece.

8. The device of claim 7 wherein the filter is replaceable.

9. The device of claim 6 further comprising a block preventing smoke from reaching the mouthpiece.

10. A method of smoking smokable material comprising:
    a) selecting the device of claim 5;
    b) placing smokable material into the burning section of the housing;
    c) igniting the placed smokable material; and
    d) inhaling smoke from the smokable material through the mouthpiece.

11. The method of claim 10 further comprising rotating the rotatable shaft for driving some of the smokable material towards the second end of the housing.

12. A device for smoking smokable material comprising:
a housing having a first end, a second end, a burning section proximate to the first end, an inhalation section proximate to the second end, and a longitudinal axis, wherein the first end is open, and wherein the burning section is sized and shaped for receiving smokable material inserted through the first end of the housing;
a shaft adapted for driving the smokable material toward the second end of the housing, the shaft comprising a worm gear spiral groove with an axial hole and a plurality of parallel radial holes passing through and perpendicular to the axial hole formed therein;
a mouthpiece formed separately from the housing and positioned to receive smoke;
a pusher located in the housing and encircling and contacting the shaft;
a longitudinal opening in the mouthpiece for passing smoke through the mouthpiece; and
a connector configured to receive a threaded end of the shaft such that rotation of the mouthpiece in a first direction causes rotation of the connector and the shaft in the first direction, causing the shaft to move the pusher and the smokable material along the longitudinal axis toward the first end, and rotation of the mouthpiece in a second direction causes rotation of the connector and the rotatable shaft in the second direction, causing the shaft to move the pusher along the longitudinal axis away from the first end;
wherein combustion of the smokable material positioned around the shaft and inhalation from the mouthpiece causes smoke produced from the smokable material to pass through the plurality of parallel holes into the axial hole and to the mouthpiece.

13. A device for smoking smokable material comprising:
a housing having a first end, a second end, a burning section proximate to the first end, an inhalation section proximate to the second end, and a longitudinal axis, wherein the first end is open, and wherein the burning section is sized and shaped for receiving compressed smokable material inserted through the first end of the housing;
a shaft for driving the smokable material toward the second end of the housing, the shaft comprising a forward threaded end joined to a rearward portion comprising a worm gear spiral groove with an axial hole and a plurality of parallel radial holes passing through and perpendicular to the axial hole formed therein;
a pusher positioned about and movable by the shaft;
a mouthpiece formed separately from the housing and provided adjacent the housing; and
a connector configured to receive a threaded end of the shaft such that rotation of the mouthpiece in a first direction causes rotation of the connector and the shaft in the first direction, causing the shaft to move the pusher and the smokable material within the housing and along the longitudinal axis toward the first end, and rotation of the mouthpiece in a second direction causes rotation of the connector and the rotatable shaft in the second direction, causing the shaft to move the pusher within the housing and along the longitudinal axis away from the first end;
wherein combustion of the smokable material positioned around the shaft and inhalation from the mouthpiece causes smoke produced from the smokable material to pass through the plurality of parallel holes into the axial hole and to the mouthpiece.

14. The device of claim 13 further comprising a block for preventing smoke from the smokable material from passing to the inhalation section.

15. The device of claim 13 further comprising a barb formed at a remote end of the shaft proximate the rearward portion.

16. The device of claim 13 wherein grooves are provided along a periphery of the shaft.

17. The device of claim 13 further comprising a filter located within the mouthpiece.

18. A device for smoking smokable material, comprising:
a housing having a first end, a second end, a burning section proximate to the first end, and a longitudinal axis, wherein the first end is open;
a rotatable shaft having a forward threaded end joined to a rearward portion comprising a worm gear spiral groove with an axial hole and a plurality of parallel radial holes passing through and perpendicular to the axial hole formed therein;
a pusher in the housing for pushing the smokable material towards the first end of the housing and toward the plurality of parallel radial holes, the pusher being moveable along the longitudinal axis of the housing by the rotatable shaft and encircling the rotatable shaft in the housing;
a mouthpiece at the second end of the housing, wherein the mouthpiece is rotatable relative to the housing;
a filter in the mouthpiece; and
a connector connecting the mouthpiece to the rotatable shaft, the connector configured to receive a threaded end of the rotatable shaft such that rotation of the mouthpiece in a first direction causes rotation of the connector and the rotatable shaft in the first direction, causing the rotatable shaft to move the pusher and the smokable material within the housing along the longitudinal axis toward the first end, and rotation of the mouthpiece in a second direction causes rotation of the connector and the rotatable shaft in the second direction, causing the rotatable shaft to move the pusher within the housing along the longitudinal axis away from the first end;
wherein combustion of the smokable material positioned around the rotatable shaft and inhalation from the mouthpiece causes smoke produced from the smokable material to pass through the plurality of parallel holes into the axial hole and to the mouthpiece.

* * * * *